US006375964B1

(12) United States Patent
Cornelius

(10) Patent No.: US 6,375,964 B1
(45) Date of Patent: Apr. 23, 2002

(54) HARD SURFACE CLEANERS COMPRISING A POLYURETHANE FOAM MATRIX AND A COMPOSITE OF A SOURCE OF SILVER IONS AND POROUS SUPPORT MATERIAL

(75) Inventor: Gay Cornelius, Cottingham (GB)

(73) Assignee: Reckitt Benckiser (UK) Limited, Slough (GB)

( * ) Notice: Subject to any disclaimer, the term of this patent is extended or adjusted under 35 U.S.C. 154(b) by 0 days.

(21) Appl. No.: 09/424,899

(22) PCT Filed: Jun. 12, 1998

(86) PCT No.: PCT/GB98/01727

§ 371 Date: Nov. 30, 1999

§ 102(e) Date: Nov. 30, 1999

(87) PCT Pub. No.: WO98/59026

PCT Pub. Date: Dec. 30, 1998

(30) Foreign Application Priority Data

Jun. 20, 1997 (GB) .............................. 9713023

(51) Int. Cl.$^7$ ..................... A01N 25/00; A01N 25/08; A61F 13/00; A61K 9/70
(52) U.S. Cl. ..................... 424/404; 424/405; 424/409; 424/443
(58) Field of Search ................................ 424/400, 404, 424/405, 409, 443, 402

(56) References Cited

U.S. PATENT DOCUMENTS

| 3,283,357 | A | * | 11/1966 | Decker ........................ 15/506 |
| 4,203,857 | A | | 5/1980 | Dugan ........................ 252/92 |
| 4,476,251 | A | | 10/1984 | Cianciolo et al. ............ 521/110 |
| 4,728,323 | A | * | 3/1988 | Matson ........................ 604/304 |
| 4,734,439 | A | * | 3/1988 | Reischl ........................ 521/54 |
| 4,906,466 | A | * | 3/1990 | Edwards et al. .............. 424/78 |
| 5,413,788 | A | | 5/1995 | Edwards et al. ............. 424/409 |

FOREIGN PATENT DOCUMENTS

| NL | A 9500096 | 9/1995 | .......... A01N/25/08 |
| WO | WO97/23594 | 7/1997 | ............ C11D/3/48 |

OTHER PUBLICATIONS

Copy of PCT International Search Report for PCT/GB98/01727 dated Sep. 22, 1998.

* cited by examiner

Primary Examiner—Thurman K. Page
Assistant Examiner—S. Howard
(74) Attorney, Agent, or Firm—Fish & Richardson P.C.

(57) ABSTRACT

A cleaning material for cleansing surfaces comprises a closed cell foam matrix including an antimicrobial composition. The foam matrix may be a polyurethane foam and the antimicrobial composition may comprise a source of silver ions in the form of a composite in combination with a porous support material such as titanium dioxide.

19 Claims, No Drawings

HARD SURFACE CLEANERS COMPRISING A POLYURETHANE FOAM MATRIX AND A COMPOSITE OF A SOURCE OF SILVER IONS AND POROUS SUPPORT MATERIAL

BACKGROUND OF THE INVENTION

This invention relates to the cleansing of surfaces and more particularly, but not exclusively, is concerned with the cleansing of non-absorbent hard surfaces found in the domestic environment.

It is an object of the present invention to provide a new and improved cleaning material for cleansing a surface without scratching the surface.

SUMMARY OF THE INVENTION

According to one aspect of the present invention there is provided a cleaning material for cleansing surfaces which material comprises a coherent self-supporting body formed of a closed cell foam matrix including an antimicrobial composition which comprises a source of silver ions as antimicrobial agent, the composition being such that silver ions are released from the composition when the body is in contact with water.

In use, the surface is rubbed with the cleaning material and it is particularly preferred for the foam matrix to be of such a friability that it tends to wear away to a limited extent when being rubbed on the surface with the ingrained dirt in the cracks and fissures in the surface being rolled out by the fine nature of the mildly abrasive particles formed as the matrix crumbles in use. A rating of the friability of the foam matrix can be found using Stable Micro Systems Ltd Texture Analyser TA-XT2 in particular in conjunction with the Craft Knife Adapter & Blades Test Unit (code A/CKB). The preferred friability corresponds to a force in the range of 700–900 gms with a pre speed of 2.00 mm per second using this technique.

Accordingly, another aspect of the present invention provides a method of cleansing a surface which comprises rubbing the surface with a cleaning material as above defined in the presence of water.

DETAILED DISCLOSURE

Cellular products resulting from the foaming of certain polymers are subject to microbial attack either because the polymer is a food source of organisms or because the reticular form of the polymer allows the collection of debris which serves as a food source for the organisms. The present invention utilises a closed cell foam which is unable to absorb water and become moist. This together with the anti-bacterial composition means that the system is sanitary.

It is particularly preferred for the foam matrix to have a density of from 30 to 70 (preferably from 42 to 56 kg/m3) and a substantially uniform and fine cell size. Preferably the foam is a rigid polyurethane foam.

Preferably the source of the silver ions is a silver salt such as a silver halide, for example silver chloride.

In a preferred embodiment, the antimicrobial composition includes a support material for the source of silver ions. Preferably, the support material is porous so that it can absorb the source and protect it from ambient light. Suitable support materials are oxidic materials such as particulate titanium oxide. On contact with aqueous medium, the support material releases silver ions in a controlled way. Such supported silver compounds are described in U.S. Pat. No. 4,906,466, the disclosure of which is incorporated herein by reference.

In accordance with a particular preferred embodiment of the present invention, the support material is a composite comprising titanium dioxide having an average particle size of about 1 to 15 mm, preferably about 2 to 5 mm, and having from about 10 to 80% preferably 20 to 60%, by weight (based on the composite) of silver chloride incorporated therein.

In addition to including the source of silver ions, the composition may comprise a colourant. Suitable colourants are commercially available colourants such as "Solvent Yellow 98" from Hoechst or "Solvent Blue 70" from BASF. It will be understood, however, that the choice of colour is arbitrary and that any suitable colourant known in the art can be used. It is particularly preferred for the cleaning material to be colour coded, a particular colour being used to designate the suitability of the material for a particular cleansing task.

The antimicrobial composition is preferably uniformly incorporated into the foamed matrix.

Preferably the cleaning material is in the form of a block about 120×50×45 mm in size and shaped to fit the hand. During use, it wears away to take the shape of the contours of the surface being cleaned and this enables awkward corners to be cleaned.

When, in use, the preferred cleaning material is rubbed over the surface to be cleaned together with a little water (e.g. cold tap water), the closed cell polyurethane foam wears away providing, as it does so, sufficient abrasive particles to clean dirt out of the fissures and cracks in the surface being cleaned. At the same time, silver ions are leached out of the composition to provide disinfection. As the foamed matrix is a closed cell structure, water will only come into contact with the silver ion source when a fresh surface is exposed due to the shearing action on the block as it is rubbed over the surface to be cleaned. After cleaning, the surface is wiped over with a cloth to finish. This removes residues created by the cleaning action but leaves sufficient silver composite within the surface fissures to provide the antimicrobial action. As more water is added to the surface, so residual antimicrobial action occurs.

The cleaning material of the present invention is particularly suitable for cleansing surfaces such as work surfaces (especially textured melamine surfaces), sinks (especially textured plastics sinks), all types of cooker hobs (particularly vitreous ceramic hobs), oven interiors, extractor fan exterior surfaces, kitchen appliances (particularly those with textured plastic surfaces), windows and mirrors, baths and washbasins, tiles and marble, and non-absorbent floor tiles.

The following Example illustrates the invention.

EXAMPLE

A free-flowing titanium dioxide/silver chloride composite powder was prepared by reacting silver nitrate with sodium chloride in the presence of titanium dioxide particles having an average size of from about 2 to 3 mm so that, after drying, the composite contained 20% by weight silver chloride and 80% by weight titanium dioxide.

A polyurethane foam was made from a stoichiometric excess of commercial grade diphenylmethane 4,4'-diisocyanate (MDI) and a polyol and the above composite was incorporated therein. The foam was processed by dispensing it through a machine into a mould to obtain a block comprising a fine and regular closed cell foam matrix containing not more than 4% by weight of the composite and having a density in the range of from 30 to 70 kg/m3.

A surface of the block was rubbed over a hard non-absorbent surface to be cleaned in the presence of cold tap water. The block surface abraded away slightly to form abrasive particles which effectively removed dirt from the fissures and cracks in the surface to be cleaned. Also, the surface was disinfected by silver ions leached from the cells at the block surface. During use of the block, a fresh cleaning and disinfecting surface was continually generated as the block abraded away. After being rubbed with the block, the cleaned surface may be wiped with a damp cloth whereby the antimicrobial action continues.

What is claimed is:

1. A cleaning material for cleansing a non-absorbent surface, which material comprises a coherent self-supporting body formed of a closed cell friable foam matrix into which is incorporated an antimicrobial composition which comprises a source of silver ions as antimicrobial agent, the composition being such that silver ions are released from the composition when the body is in contact with water, said foam matrix having a friability rating corresponding to a force in the range of from 700 to 900 grams with a pre-speed of 2.00 mm per second using Stable Micro Systems Texture Analyser TA-XT2 with a Craft Knife Adapter & Blade Test Unit code A/CKB.

2. A cleaning material as claimed in claim 1, wherein the foam matrix is a closed cell polyurethane foam.

3. A cleaning material as claimed in claim 2, wherein the foam has a density of from 30 to 70 kg/m$^3$.

4. A cleaning material as claimed in claim 3, wherein the foam has a density of from 42 to 56 kg/m$^3$.

5. A cleaning material as claimed in claim 1, wherein the silver ion source is present in combination with a support material.

6. A cleaning material as claimed in claim 5, wherein the support material is a porous oxidic material.

7. A cleaning material as claimed in claim 6, wherein the support material is particulate titanium dioxide.

8. A cleaning material as claimed in claim 7, wherein the titanium dioxide has an average particle size of from 1 to 15 mm.

9. A cleaning material as claimed in claim 8, wherein the titanium dioxide has an average particle size of from 2 to 5 mm.

10. A cleaning material as claimed in claim 1 wherein the source of silver ions is a silver salt.

11. A cleaning material as claimed in claim 10, wherein the silver salt is silver chloride.

12. A cleaning material for cleansing a non-absorbent surface, which material comprises a closed cell polyurethane foam matrix into which is incorporated a composite of silver chloride as an antimicrobial agent and particulate titanium dioxide as a support material, said foam matrix having a friability rating corresponding to a force in the range of from 700 to 900 grams with a pre-speed of 2.00 mm per second using Stable Micro Systems Texture Analyser TA-XT2 with a Craft Knife Adapter & Blade Test Unit code A/CKB.

13. A cleaning material as claimed in claim 12 in which the silver chloride is present in an amount of from 10 to 80% by weight based on the weight of the composite.

14. A cleaning material as claimed in claim 13 wherein the titanium dioxide has an average particle size of from 1 to 15 mm.

15. A cleaning material as claimed in claim 14 wherein the titanium dioxide has an average particle size of from 2 to 5 mm.

16. A cleaning material as claimed in claim 15 wherein the amount of silver chloride is from 20 to 60% by weight based on the weight of the composite.

17. A cleaning material as claimed in claim 12 in which the composite material is present in an amount not exceeding 4% by weight of the closed cell polyurethane foam.

18. A method of cleansing a surface which comprises rubbing, in the presence of water, the surface with a cleaning material comprising a coherent self-supporting body formed of a closed cell friable foam matrix into which is incorporated a composite which comprises a source of silver ions as an antimicrobial agent in combination with a support material, the composition being such that silver ions are released from the composition which the body is in contact with water, said foam matrix having a friability rating corresponding to a force in the range of from 700 to 900 grams with a pre-speed of 2.00 mm per second using Stable Micro Systems Texture Analyser TA-XT2 with a Craft Knife Adapter & Blade Test Unit code A/CKB.

19. A method according to claim 18 in which the closed cell friable foam matrix is polyurethane foam, the antimicrobial agent is silver chloride and the support material is particulate titanium dioxide.

* * * * *